US00PP33727P2

(12) United States Plant Patent
Van Swieten

(10) Patent No.: US PP33,727 P2
(45) Date of Patent: Dec. 7, 2021

(54) ***PHALAENOPSIS* ORCHID PLANT NAMED 'PHALBIRWIN'**

(50) Latin Name: ***Phalaenopsis* hybrid**
Varietal Denomination: PHALBIRWIN

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,386

(22) Filed: Jun. 10, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALBIRWIN', particularly characterized by small, reddish-purple flowers with light reddish-purple centers and dark red-purple lips, dorsal sepals with an incurving curvature of the longitudinal axis, a short and compact plant having five to seven branches, and is propagated by meristem tissue culture, is disclosed.

3 Drawing Sheets

Genus and species: *Phalaenopsis* hybrid.
Variety denomination: 'PHALBIRWIN'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALBIRWIN'.

The new *Phalaenopsis* plant is a product of a planned breeding program conducted by the inventor in Bleiswijk, the Netherlands. The objective of this breeding program was to create a new, short *Phalaenopsis* plant with few branches and numerous attractive and unique, small, reddish-purple flowers with light reddish-purple centers and dark red-purple lips, suitable for potted plant production.

The new *Phalaenopsis* plant 'PHALBIRWIN' is a result of cross-pollination made by the inventor in January 2013 in Bleiswijk, the Netherlands, of the proprietary female, or seed parent, *Phalaenopsis* hybrid '17956-06' (unpatented) with the proprietary male, or pollen parent, *Phalaenopsis* hybrid '01-3389' (unpatented).

The new *Phalaenopsis* was selected by the inventor as a single plant within the progeny of the stated cross-pollination in a controlled greenhouse in Bleiswijk, the Netherlands, in November 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 30, 2020 (Application no. 2020/0305), by Applicant who obtained the subject matter disclosed directly from the inventor. 'PHALBIRWIN' has not been made publicly available or sold anywhere in the world prior to the effective filing date of this application with the exception of sales or disclosures made one year or less before the effective filing date of this claimed invention by Applicant who obtained 'PHALBIRWIN' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALBIRWIN' as a new and distinct variety of *Phalaenopsis* plant:

1) Small, reddish-purple flowers with light reddish-purple centers and dark red-purple lips;
2) Curvature of the longitudinal axis of the dorsal sepal is incurving;
3) Plant has 5 to 7 branches; and
4) Plant is short and compact.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 42-week-old plants in February 2021. Colors in the photographs may differ from the color values cited in the detailed botanical description, which accurately describe the actual colors of the new variety.

DESCRIPTION OF THE NEW VARIETY

Figure 1:
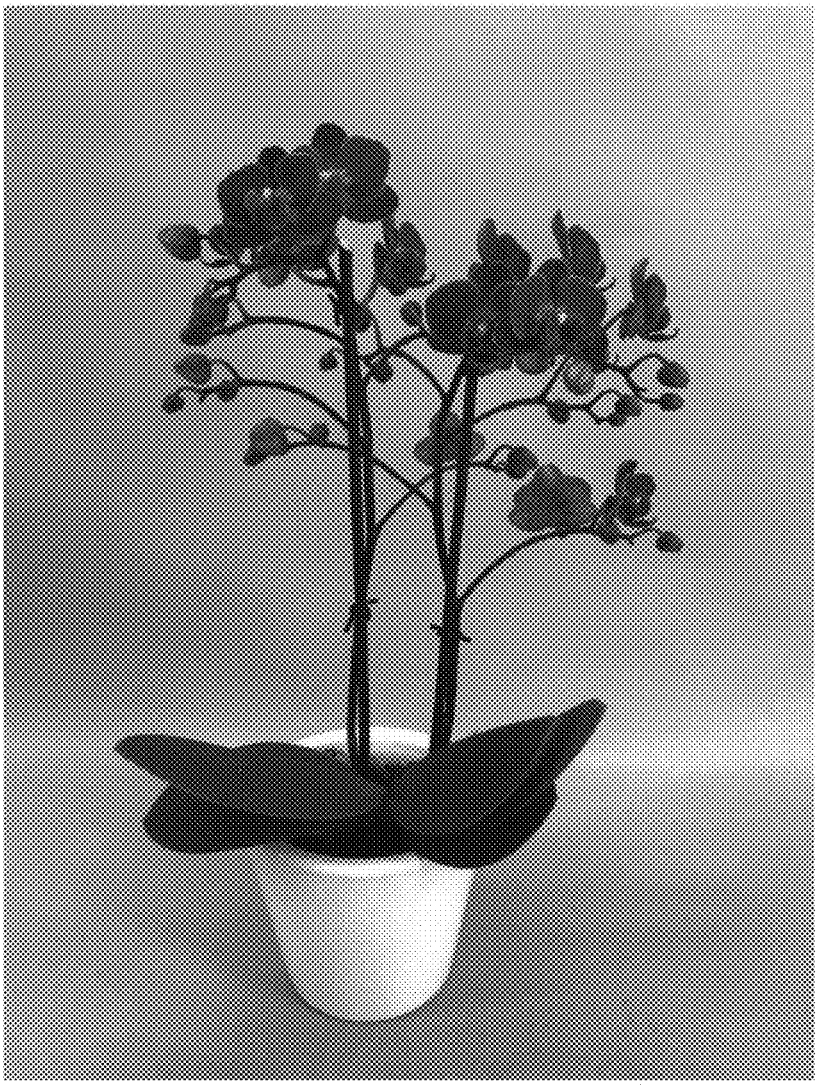
FIG. 1 shows the overall plant habit, including blooms, buds, and foliage of 'PHALBIRWIN'.
Figure 2:
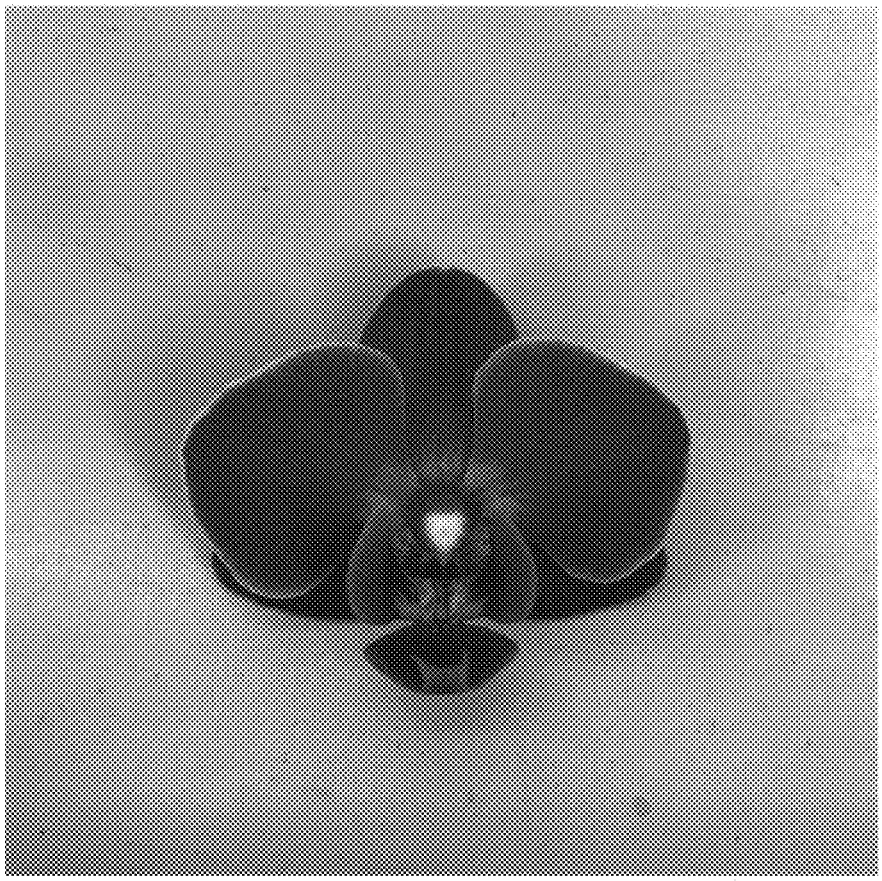
FIG. 2 shows a close-up of a flower of 'PHALBIRWIN'.
Figure 3:
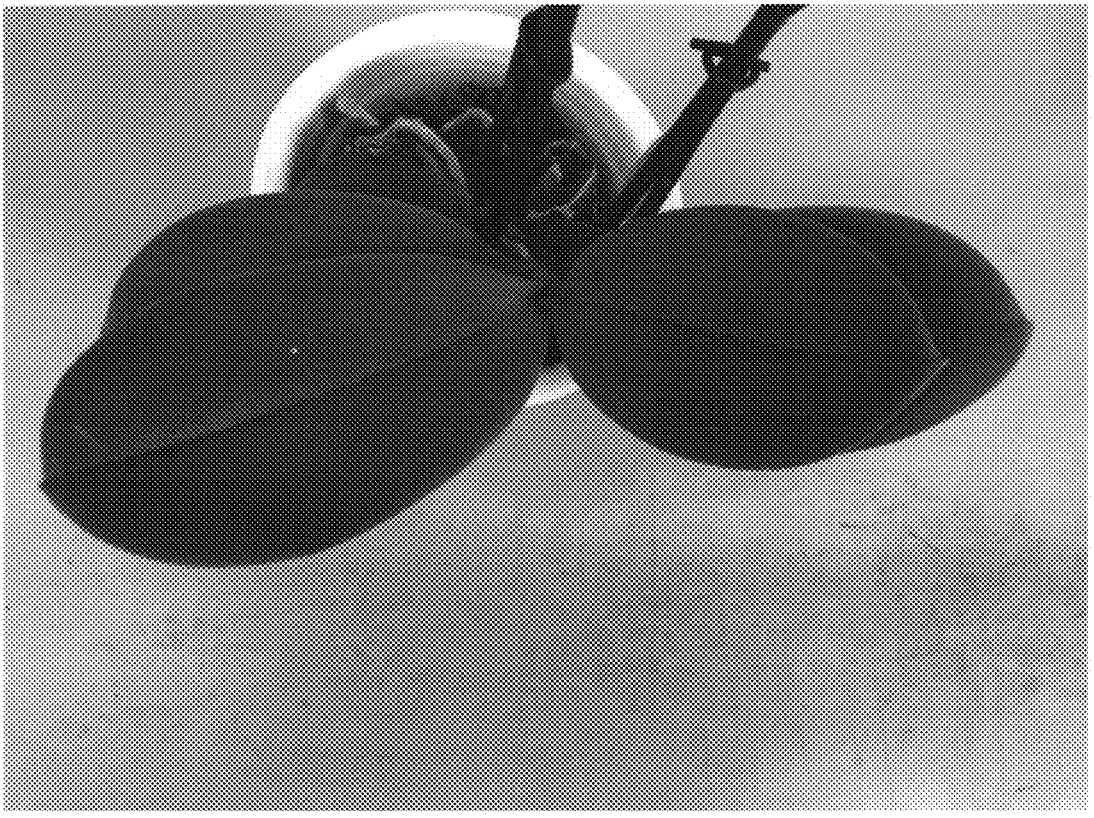
FIG. 3 shows an overhead view of the leaves of 'PHALBIRWIN'.

The following detailed description sets forth the distinctive characteristics of 'PHALBIRWIN'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2021 on flowering plants which were planted in 9-centimeter (diameter) pots. After in vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALBIRWIN'.

Parentage:
- *Female parent*.—*Phalaenopsis* cultivar '17956-06' (unpatented).
- *Male parent*.—*Phalaenopsis* cultivar '01-3389' (unpatented).

Propagation:
- *Type*.—Meristem tissue culture.

Roots:
- *Root description*.—Greyed-green (a color in between RHS 190B and RHS 190C) colored roots with a touch of purplish-red (RHS N77B) and branching lateral roots having yellow-green (RHS N144A) colored root tips.

Plant:
- *Crop time to flowering*.—Following asexual propagation (in vitro), the rooted cuttings grow for 18-20 weeks. After transplantation into 9-cm pots, the plants are finished after 40 to 42 weeks.
- *Growth habit of the peduncle*.—Upright to slightly pendent with panicle inflorescence.
- *Height* (*from soil level to top of inflorescence*).—Approximately 25.0 cm to 30.0 cm.
- *Width* (*measured from leaf tips*).—About 18.0 cm to 21.0 cm.
- *Vigor*.—Strong.

Leaves:
- *Mature leaves*.—Quantity per plant: 7 to 8 leaves are produced before flowering. Length (fully expanded): 10.0 cm to 12.0 cm. Width: 5.5 cm to 6.5 cm. Position of the broadest part of the leaf: At the middle. Shape: Oblong. Base shape: Moderately to slightly elongated. Apex: Obtuse slightly asymmetric. Leaf blade angle with the petiole (measured from the horizontal position): Between 15 degrees and 35 degrees. Leaf margin: Entire. Color: Upper surface: RHS 146A. Lower surface: RHS 146B. Texture (both upper and lower surfaces): Smooth. Thickness: 1.8 mm to 2.1 mm. Variegation: Absent. Venation: Pattern: Parallel. Color of the midvein: Upper surface: RHS 146A. Lower surface: RHS 146B.

Peduncle:
- *Quantity per plant*.—1 to 3.
- *Number of flowers per peduncle*.—14 to 24.
- *Length*.—25.0 cm to 30.0 cm.
- *Diameter*.—3.0 mm to 4.0 mm.
- *Strength*.—Strong.
- *Aspect*.—Upright to slightly pendent.
- *Texture*.—Smooth.
- *Color*.—Dark reddish-brown (a color in between RHS 187A and RHS 200B).
- *Internode length*.—1.0 cm to 2.0 cm.

Inflorescence description:
- *Appearance*.—Upright to slightly pendent, panicle inflorescence with bilaterally symmetrical flowers that open in succession beginning with the lowermost flower.
- *Number of inflorescences*.—1 to 3.
- *Inflorescence size*.—Height (from base to tip): 120.0 mm to 150.0 mm.
- *Flowering time*.—First flowers can be expected 7 to 8 months after planting in a 9-cm pot.
- *Flower*.—Height: 30.0 mm to 35.0 mm. Diameter: 40.0 mm to 45.0 mm. Depth of lip: About 13.0 mm to 15.0 mm.
- *Flower longevity*.—On the plant: 11 to 13 weeks.
- *Flower shape*.—Flat.
- *Fragrance*.—Absent.
- *Flower bud*.—Average size: Medium. Length: 14.0 mm to 16.0 mm. Width: 12.0 mm to 14.0 mm. Shape: Egg shaped. Color: Yellow-green (RHS 146C) with dark purplish-red stripes and shade (RHS N79B).
- *Petals*.—Arrangement: Open/free. Shape: Semi-circular. Apex: Obtuse asymmetric. Margin: Entire. Length (from base to tip): 19.0 mm to 21.0 mm. Width: 22.0 mm to 24.0 mm. Position of the broadest part of the petal: At the base. Color (when fully opened): Upper surface: Basic color: Reddish-purple (a color in between RHS N78A and RHS N79C). Over color: Light reddish-purple (RHS N78D) at the base; dark purplish-red stripes (RHS N79C) and very light purple small edge (RHS 76B). Lower surface: Basic color: Reddish-purple (RHS N78B). Over color: Light reddish-purple (RHS N78D) at the middle and small very light purple edge (RHS 76B). Number of spots and stripes on the petals (upper surface): Medium to many stripes. Color of spots and stripes on the petals (upper surface): RHS N79C. Density of netting of the petals (upper surface): None. Color of the netting (upper surface): None.
- *Dorsal sepal*.—Shape: Broad elliptic. Apex: Emarginated symmetric. Margin: Entire. Length (from base to tip): 19.0 mm to 21.0 mm. Width: 17.0 mm to 19.0 mm. Position of the broadest part of the dorsal sepals: At the middle. Color (when fully opened): Upper surface: Basic color: Reddish-purple (a color in between RHS N78A and RHS N79C). Over color: Light reddish-purple (RHS N78D) at the base; dark purplish-red stripes (RHS N79C) and very light purple small edge (RHS 76B). Lower surface: Basic color: Reddish-purple (a color in between RHS N78B and RHS N78C). Over color: Light purple (a color in between RHS 76A and RHS N78D). Number of spots and stripes on the dorsal sepals (upper surface): Medium stripes. Color of spots and stripes on the dorsal sepals (upper surface): RHS N79C. Density of netting of the dorsal sepals (upper surface): None. Color of the netting (upper surface): None.

*Lateral sepals*.—Shape: Ovate. Apex: Obtuse asymmetric. Margin: Entire. Length (from base to tip): 21.0 mm to 23.0 mm. Width: 16.0 mm to 18.0 mm. Position of the broadest part of the lateral sepals: Toward the base. Color (when fully opened): Upper surface: Basic color: Reddish-purple (a color in between RHS N78A and RHS N79C). Over color: Touch of yellow-green (RHS 145C) with very small dots (RHS 59B) at the base; stripes and netting (RHS N79C). Lower surface: Basic color: Reddish-purple (a color in between RHS N78B and RHS N78C). Over color: Yellowish-green (RHS 145C) at the base; light purple (a color in between RHS 76A and RHS N78D) at the middle toward the tip and reddish-purple midvein (RHS N78A) toward the tip. Number of spots, dots, and stripes on the lateral sepals (upper surface): Few dots at the base; medium stripes. Color of spots, dots, and stripes on the lateral sepals (upper surface): Dots (RHS 59B); stripes (RHS N79C). Density of netting of the lateral sepals (upper surface): Medium. Color of the netting (upper surface): RHS N79C.

*Labellum* (*lip*).—Whiskers: Present, but very short. Length of whiskers: 1.0 mm to 2.0 mm. Color of whiskers: Dark purplish-red (RHS N79C) with little white tips (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Slightly undulated. Length: 13.0 mm to 15.0 mm. Width: 8.0 mm to 10.0 mm. Color: Upper surface: Touch of yellow (RHS 13A) at the base; dark red stripes (RHS 187A); dark red (RHS 187A) and purplish-red (a color in between RHS 59B and RHS 59C) toward the tip. Lower surface: Yellowish-white (RHS 155D) at the base; purplish-red (RHS 59B) on one side and purplish-red (RHS 59C) toward the other side and tip. Number of spots and stripes on the lateral lobe: Medium stripes. Color of spots and stripes on the lateral lobe: RHS 187A. Density of netting of the lateral lobe: None. Color of the netting: None.

*Apical lobe*.—Shape: Circular. Margin: Entire. Length: 15.0 mm to 17.0 mm. Width: 11.0 mm to 13.0 mm. Color: Upper surface: Touch of yellow (RHS 12A) at the base; dark red (a color in between RHS 187B and RHS 187C); dark purplish-red (RHS N79C) toward margin and whiskers. Lower surface: Yellowish-white (RHS 155B) at the middle from the base toward whiskers; light yellow (RHS 12C) and dark red (RHS 187C) toward wings; dark red-purple (a color in between RHS N79C and RHS N79D) toward margins and whiskers. Number of spots and stripes on the apical lobe: None. Color of spots and stripes on the apical lobe: None. Density of netting of the apical lobe: None. Color of the netting: None. Bump and ridge: Absent.

*Callus*.—Average size: Small. Height: 3.0 mm to 4.0 mm. Length: 4.0 mm to 5.0 mm. Width: 3.0 mm to 4.0 mm. Color: Yellow tips (RHS 12A); light greenish-yellow (RHS 8C) on sides; dotted (RHS 59B).

Reproductive organs:

*Column*.—Length: 6.0 mm to 8.0 mm. Diameter: 3.0 mm to 4.0 mm. Color: Reddish-purple (RHS N78B) on sides and (RHS N78A) at the middle.

*Pollinia*.—Quantity: 2. Diameter: 0.7 mm to 0.9 mm. Color: Orange (RHS 24A).

*Ovary*.—Length: 8.0 mm to 10.0 mm. Diameter: 1.5 mm to 1.7 mm.

*Pedicel*.—Length: 25.0 mm to 27.0 mm. Diameter: 1.8 mm to 2.0 mm. Color: Touch of dark red (RHS 187B) at the base; yellow-green (RHS 195B) and reddish-purple (RHS N78B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALBIRWIN' differs from the female parent plant '17956-06' (unpatented) in that 'PHALBIRWIN' has obtuse petal apexes and weak curvature of the lateral lobes, whereas '17956-06' has rounded petal apexes and medium curvature of the lateral lobes. Additionally, 'PHALBIRWIN' has smaller flowers than '17956-06'.

'PHALBIRWIN' differs from the male parent plant '01-3389' (unpatented) in that 'PHALBIRWIN' has circular apical lobes and whiskers, whereas '01-3389' has ovate apical lobes and no whiskers.

'PHALBIRWIN' is most similar to the commercial *Phalaenopsis* plants named 'PHALFEMYM' (U.S. Plant Pat. No. 29,783) and 'PHALFITYJA' (U.S. Plant Pat. No. 31,978). 'PHALBIRWIN' differs from the commercial variety 'PHALFEMYM' in that 'PHALBIRWIN' has a flat flower shape in lateral view, circular apical lobes, and weak curvature of the lateral lobes, whereas 'PHALFEMYM' has a concave flower shape in lateral view, ovate apical lobes, and medium curvature of the lateral lobes.

'PHALBIRWIN' differs from the commercial variety 'PHALFITYJA' in that 'PHALBIRWIN' has emarginated dorsal sepal apexes and circular apical lobes, whereas 'PHALFITYJA' has obtuse dorsal sepal apexes and ovate apical lobes. Additionally, 'PHALBIRWIN' has wider dorsal sepals than 'PHALFITYJA'.

I claim:

1. A new and distinct variety of *Phalaenopsis* plant named 'PHALBIRWIN', substantially as described and illustrated herein.

* * * * *